United States Patent [19]

Ito

[11] Patent Number: 4,573,472

[45] Date of Patent: Mar. 4, 1986

[54] AUTOGENIC TRAINING AND TREATING APPARATUS

[76] Inventor: Yoshihiro Ito, 7-1 and 8 Gacchi, Imachi, Hanazono, Ukyo-ku, Kyoto, Japan

[21] Appl. No.: 421,643

[22] Filed: Sep. 22, 1982

[30] Foreign Application Priority Data

Sep. 25, 1981 [JP] Japan .................................. 56-152417
Mar. 15, 1982 [JP] Japan .................................. 57-41413

[51] Int. Cl.⁴ .............................................. A61F 7/00
[52] U.S. Cl. ................................... 128/399; 128/670; 128/804; 434/262
[58] Field of Search ....................... 128/731, 732, 905; 434/262; 119/29

[56] References Cited

U.S. PATENT DOCUMENTS 4,216,781  8/1980  John .

OTHER PUBLICATIONS

*Handbook of Clinical Behavior Therapy*, Wiley Series on Personality Processes, 1981, Chap. 14, 15, p. 643.
"Autogenic Therapy" Wolfgang Luthe, pp. 14–21.
"Yoga and Medicine" Steven Brena, pp. 248–251.

Primary Examiner—Kyle L. Howell
Assistant Examiner—Francis J. Jaworski
Attorney, Agent, or Firm—Morgan, Finnegan, Pine, Foley & Lee

[57] ABSTRACT

A medical apparatus for making a subject learn the method of autogenic training and thereby treat an affected disease himself is disclosed.

The apparatus can provide informing signals and physical stimuli to a subject, said signals and said stimuli are generated substantially in synchronism with each other for informing the subject with stimulus timing, and applying the stimulus to a concerned part of his body, respectively. Early in the sequence of such timing, the stimulus is completely correspondingly generated with the signal, meanwhile the stimulus is sometimes absent from the correspondence with the signal. In each of the stimulus absent times a significant bio-reaction is also caused by a conditioned reflex in the subject's physiology. This reaction is substantially the same to the normal reaction in the stimulus generating time. This will be connected with the self-learning of an associated autogenic training of the subject.

The stimuli may comprise a therapeutic stimulus to a diseased part and a negative stimulus to reduce the therapeutic effect of the former. The therapeutic stimulus is sometimes absent from a stable timing for aiding the autogenic training of the subject.

20 Claims, 18 Drawing Figures

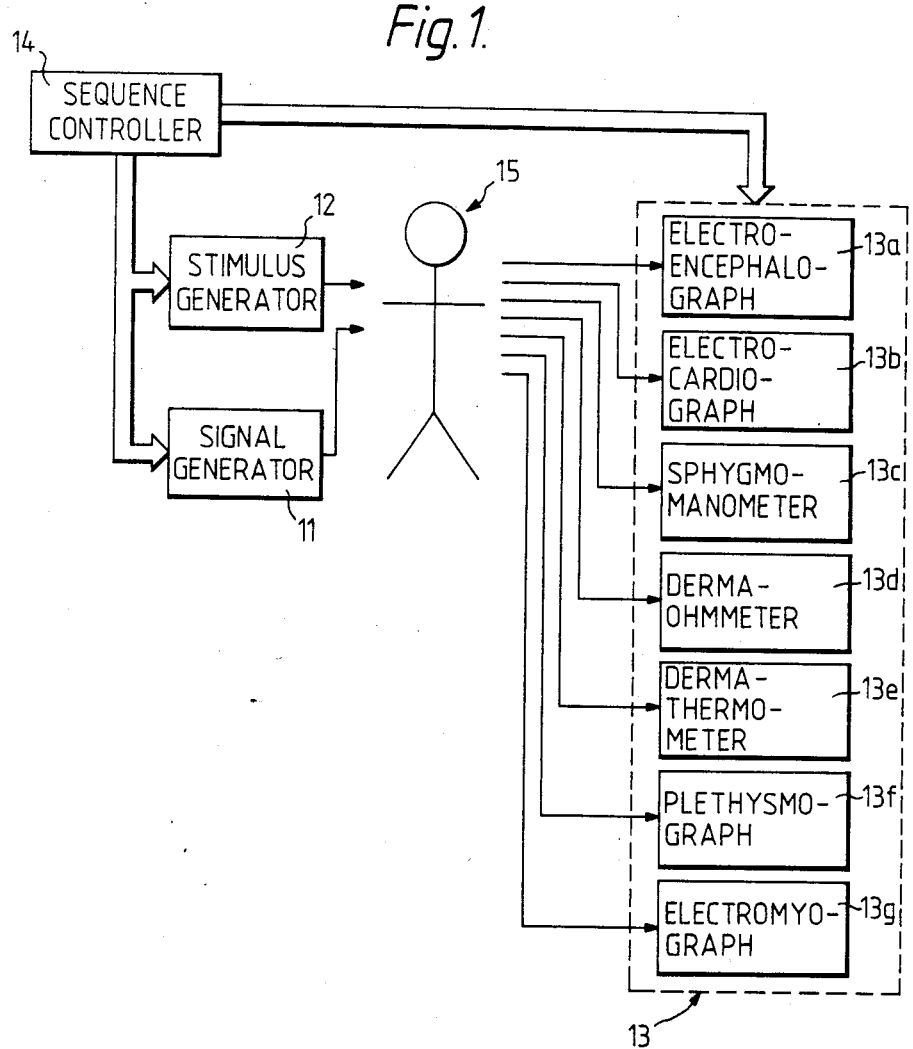

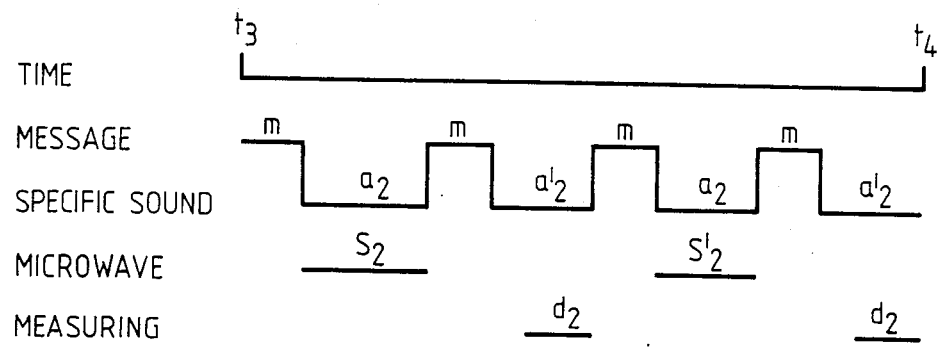
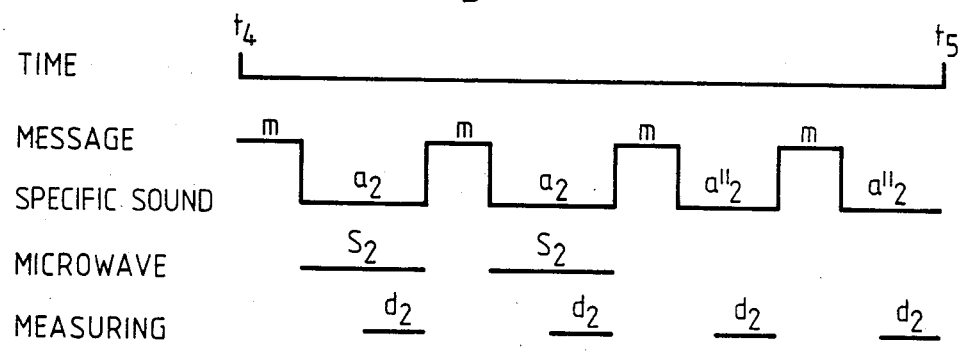

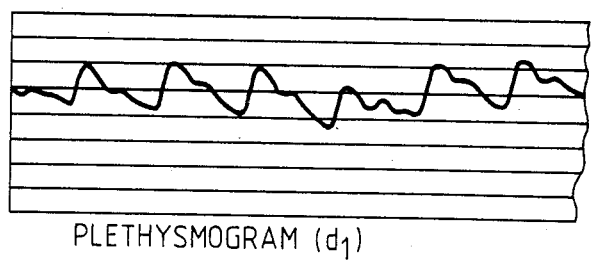
Fig.3A.
PLETHYSMOGRAM ($d_1$)
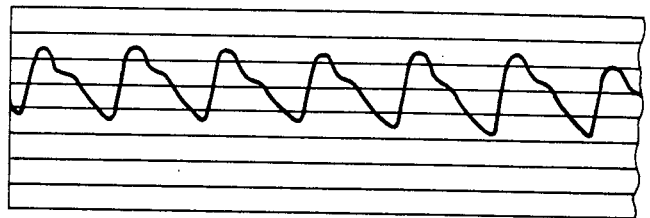
Fig.3.B.
PLETHYSMOGRAM ($s_1$ OR $s_2$)
Fig.3C.
PLETHYSMOGRAM ($a'_2$ OR $a''_2$)
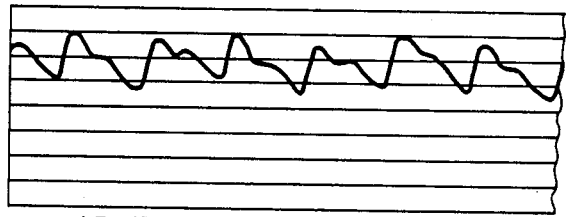
Fig.3D.
AFTER THE SEQUENCES
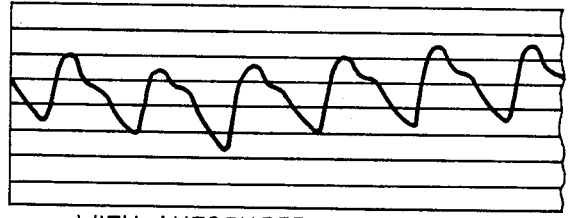
Fig3E.
WITH AUTOSUGGESTION

AUTOGENIC TRAINING AND TREATING APPARATUS

BACKGROUND OF THE INVENTION

The present invention relates to an apparatus for aiding a subject to learn the autogenic training and treat his disease.

In recent years, the autogenic training, developed on the principle of hypnosis, has been widely utilized in clinical applications of psychosomatics. The autogenic training is a method using autohypnosis to remedy and control disorder of the autonomic nervous system due mainly to mental stresses, thereby curing psychosomatic diseases. It was advocated by Dr. Schultze, Germany, and completed by Dr. Luthe, Canada.

The general formula for the autogenic training consists in a subject, who is at ease, subjecting himself to autosuggestion, such as (1) I feel warm in my right hand, (2) my heart is beating very quietly, (3) I am breathing comfortably, (4) I feel warm in or around my stomach, and (5) I feel cool in my forehead, and training himself to assume these mental states, until he becomes autohypnotic. That is, it consists in lowering the conscious level to the unconscious to dispel mental depression.

This method, however, has a fatal defect in that an autosuggested mental state, e.g., "I feel warm in my right hand" results in the active concentration of attention, which contrarily tends to lower the temperature of the right hand: thus, attainment of the expected result of autosuggestion requires the passive concentration of attention, which is regarded as very difficult to attain (refer to "Autogenic Therapy" by Wolfgang Luthe).

The principal object of the invention is to provide an autogenic training and treating apparatus which applies the theory of conditioned refléx to aiding in easily learning the autogenic training, which involves the foregoing difficulty.

Another object of the invention is to provide an autogenic training and treating apparatus adapted to treat a subject's disease, particularly to remove his local pain, thereby remedying lack of psychosomatic coordination.

SUMMARY OF THE INVENTION

In brief, the apparatus of the present invention basically comprises intermittent signal generating means for regularly giving a subject signals consisting of predetermined visual and acoustic stimuli or messages, stimulus generating means for giving physical or chemical stimuli to a subject, and sequence control means for sequentially driving said signal generating means and said stimulus generating means, the arrangement being such that during the intermittent generation of said signals, said stimuli are generated in early stages in association with said signals but after the lapse of a predetermined time there is incorporated a period of time in which said physical or chemical stimuli are omitted. In this case, if a series of voice messages, e.g., "I feel warm in my right hand" are intermittently produced as said signals while physical or chemical stimuli to enforce the contents of the massage externally of the body, e.g., microwave radiation to the right hand, for heating, are regularly produced in early stages during the intervals between successive messages and then omitted between times, the subject will become conscious of a rise in the temperature of his right hand even in the absence of said microwave radiation. That is, he has learned the autogenic training. This is because a circuit of conditioned reflex is established in the subject's nervous system by the regular association between the early messages and microwave radiation.

According to another embodiment of the present invention, said autogenic training and treating apparatus incorporates automatic measuring and recording equipment for measuring the subject's reactions in parallel with the generation of said signals and stimuli in order for the doctor or subject to check the progress of the autogenic training to see if there is an undesirable abnormal reaction, thus serving for an investigation of the training program.

An autogenic training and treating apparatus according to a further embodiment of the invention comprises first stimulus generating means for applying therapeutic stimuli based on physiotherapy and having therapeutic effects on affected parts, second stimulus generating means for applying negative stimuli to reduce said therapeutic effects, and sequence control means for sequentially controlling said first and second stimulus generating means. The sequence control means controls said first and second means in two stages, wherein (1) in the first stage, therapeutic stimuli and negative stimuli are generated simultaneously, rhythmically and intermittently in such an intensity relation that the therapeutic effects of the former are predominant, and (2) in the second stage, said therapeutic stimuli are intermittently omitted from the cycle of said rhythmical stimulus application.

According to this arrangement, since the subject regularly receives negative stimuli and therapeutic stimuli predominant thereover in the first stage, he will experience reactions as therapeutic effects, such as comfort or relief from local pain due to accelerated blood circulation. These regular reactions will also appear in the second stage with the cycle in which the therapeutic stimuli are omitted, provided the number of stimulation times during the first stage is sufficiently high. The reason for this is that the basis of conditioned reflex has been established in the body in the first stage, but what is to be noted is that the negative stimuli to the disease contrarily bring about therapeutic reactions. Therefore, under normal conditions with the negative stimuli removed, it is possible to expect a stronger therapeutic effect.

Accordingly, even if the subject who has undergone the stimulus sequence including the first and second stages returns to an environment which is not desirable to his disease, he will be able to produce a reaction leading to a cure by controlling the autonomic function by remembering the rhythm of said stimulus application.

In a more specific arrangement of the invention, it includes rhythm signal generating means for giving a subject at least one kind of signal consisting of audible or visible signals, messages or music. Such rhythm signals are synchronous with said stimulus cycle and capable of accelerating temporary connection in the body as an effect of outstanding conditional stimuli and making it possible to expect peculiar psychological effects.

The invention will now be described with reference to the accompanying drawings showing preferred embodiments thereof.

BRIEF DESCRIPTION OF THE DRAWINGS

FIG. 1 is a block diagram showing an example of the arrangement of an apparatus of the invention;

FIGS. 2A through 2E is a sequence operation diagram for the apparatus of FIG. 1;

FIGS. 3A through 3E are graphs showing plethysmograph or volume pulse waves in a subject's right hand before, during and after application of the apparatus of the invention;

DETAILED DESCRIPTION OF THE PREFERRED EMBODIMENTS

Figure 2A:
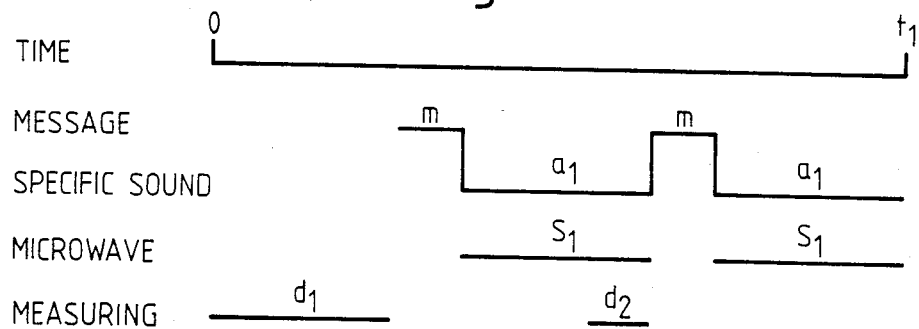

FIG. 1 shows an autogenic training and treating apparatus constructed on the basic principle of the present invention. This apparatus comprises a signal generator 11, a stimulus generator 12, an automatic measuring instrument 13, and a sequence controller 14 for sequence-controlling these devices. The signal generator 11 comprises recording means such as a magnetic tape recorder having recorded thereon a voice message which, in this case, is "I feel warm in my right hand" repeated at regular intervals of time, and a sound inserted between said messages to give notice of the actuation of the stimulus generator 12 or to be the actuation sound itself, and a headphone for subjects. If the headphone is replaced by a speaker unit, then the actuation sound of the stimulus generator 12 directly reachs the subject's ears. Thus, it is preferred that in such a stimulus time the actuation sound be used as the inserted sound between the messages, and that during omission of stimuli when the stimulus generator 12 is not actuated in the latter half of the sequence a similar sound to the actuation be produced by the speaker unit. The signal generator 11 may be so arranged that it produces an optical signal such as flashlight discernible by the subject, simultaneously with the actuation sound of the stimulus generator 12 (including said imitation sound).

The stimulus generator 12, in this embodiment, uses a microwave generator for heating the subject's part to be treated (in this case, the right hand) on the principle of microwave heating. This microwave generator 12 is commercially available for use for therapeutic purposes and is typically so arranged as to radiate 2,400 MHz electromagnetic waves to a subject's right hand about 10 cm away. In addition, the stimulus generating means 12 is not limited to such microwave radiation means, and use may be made, separately or in combination, of a drop infusion setup for infusing a solution of medicines into a subject, a cooler, a fan, and other various physical and chemical stimulating means.

The automatic measuring and recording equipment 13, as can be clearly seen in FIG. 1, comprises an electroencephalograph 13a, an electrocardiogram monitor 13b, a sphygmomanometer 13c, a dermaohmmeter 13d, a dermathermometer 13e, a plethysmograph 13f, and an electromyogram monitor 13g, the measuring electrodes of these instruments being selectively set on the body of a subject 15 so that his reactions can be automatically monitored in connection with a signal sequence given to the subject 15.

The sequence controller 14 serves to drive (on-off control) said signal generator 11, stimulus generator 12 and automatic measuring instrument 13 according to various sequence programs. An example of a basic sequence program is shown in FIGS. 2A through 2E.

Figure 2B:
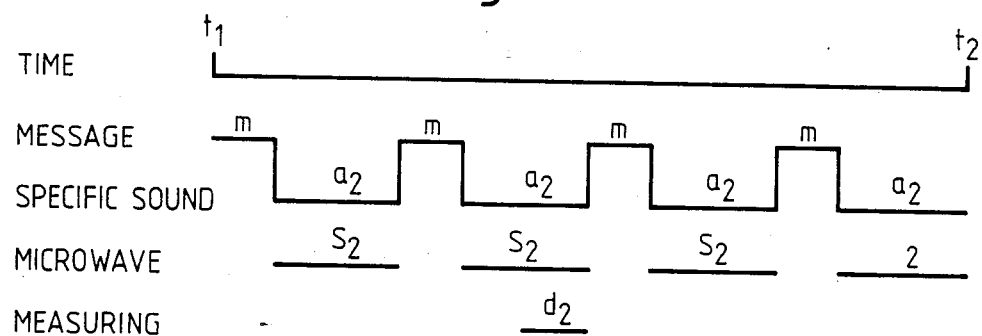
Figure 2C:
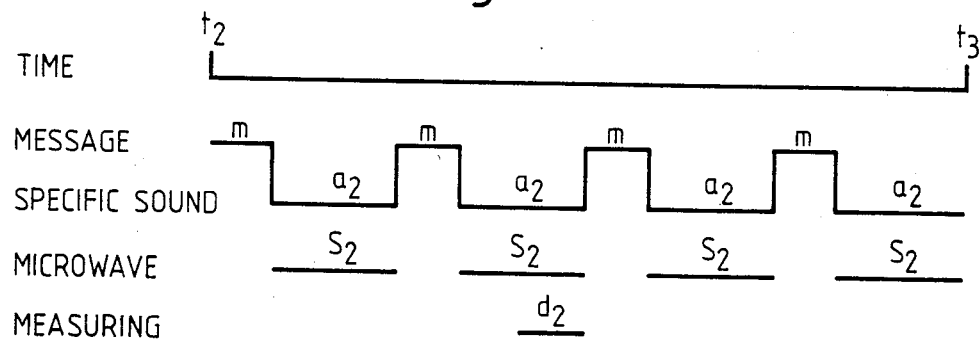

FIGS. 2A-C show regular stimulus application timing immediately after the start of the basic sequence, the initialization being made during time $d_1$ shown lower left in FIG. 2A. The time $d_1$ is about 15–20 seconds immediately after the start of the sequence and during this time are made the initialization of the measuring instrument, the power source-standby for other devices, and, if necessary, measurements of the initial values concerning a subject. The sequence initially set during time $d_1$ initiates a repetitive signal cycle m-a cycle) consisting of message time m and time a for the mechanical sound or specific sound of the stimulus generator. In the case of a voice, e.g., "I feel warm in my right hand", the message time m is estimated to be some seconds. The specific sound time a is the time during which microwave stimulation is effected subsequent to the message or is the time during which microwave stimulation is omitted, with the time a coinciding with the microwave radiation time s as shown in FIGS. 2A–2C. Two specific sound times $a_1$ and the corresponding microwave times $s_1$ immediately after the start of the sequence are estimated to be about 15 seconds (FIG. 2A), while the subsequent specific sound times $a_2$ and microwave times $s_2$ are generally estimated to be about 10 seconds (FIGS. 2B–2E). The reaction measuring time $d_2$ which accompanies the microwave stimulation is estimated to be about 5 seconds: it starts with the latter half of selected microwave times $s_1$ and $s_2$ and ends concurrently with the latter.

FIG. 2D shows a first microwave omission timing, wherein it is clear that during the specific sound time $a_2'$ of about 8 seconds, the corresponding microwave stimulation is absent. Such an "imitation sound" time $a_2'$ is so designed as shown in the figure that it appears from the first time after the 11th microwave radiation after the start of the sequence, and that the second one (also indicated by $a_2'$) appears after a microwave stimulation (time $s_2'$) of about 8 seconds. Such microwave omission timing may be continued, if desired, but in the embodiment it is succeeded by a second microwave omission timing shown in FIG. 2E.

As shown in FIG. 2E, the second omission timing provides two successive imitation sound times $a_2''$ after microwave stimulation has been effected twice. Such imitation sound time $a_2''$ is less than 8 seconds.

Application of the foregoing basic sequence ensures that the subject's body subjected to conditional stimuli (message and specific sound) according to the initial constant sequence comes to exhibit a conditioned reflex of the right hand's temperature rising and, through the sequence of FIGS. 2D and E, masters one stage of the autogenic training. In addition, my experiments have shown that if the described regular conditional stimulation is repeated about 10 times, temporary connection according to the rules of conditioned reflex takes place or, in other words, a conditioned reflex is established.

The results of measurements by the various instruments of the automatic measuring and recording equipment shown in FIG. 1 will now be described.

Plethysmograph Pulse Waves

Plethysmograph pulse waves are optically detected for measuring the blood flow rate of a part to be examined, the plethysmograph unit for this purpose has been widely used in the field of therapeutics.

FIGS. 3A-E are graphs showing the plethysmograph or volume pulse waves of the subject's right hand before and after and during application of said basic sequence, it being noted that an increase in plethysmograph pulse wave and hence in the blood flow rate means a rise in the temperature of the right hand. FIG. 3A shows the pulse waveform before application of microwaves (i.e., during the initializing time $d_1$ of the sequence). Comparing the same with the pulse waveform of FIG. 3B appearing during microwave radiation ($s_1$ or $s_2$ in FIGS. 2A-E) reveals an increase of more than 50%. This means a direct effect (a rise in the temperature of the right hand) of microwaves. FIG. 3C shows plethysmograph pulse waves appearing during the microwave omission time in the sequence (imitation sound time $a_2'$ or $a_2''$ in FIGS. 2A-E), and it can be seen that the size of the pulse waveform in this case is substantially the same as during microwave radiation. This is none other than the effect of said temporary connection.

FIGS. 3D and E show data on the same subject obtained after the basic sequence has been applied 20 times, showing plethysmograph pulse waves appearing before giving autosuggestion of "I feel warm in my right hand" and 10 seconds after giving the same, respectively. In this case it is seen that in FIG. 3D there are shown plethysmograph pulse waves having the same amplitude as that shown in FIG. 3A, but that in the graph of FIG. 3E where autosuggestion of "I feel warm in my right hand" is given, plethysmograph pulse waves corresponding to an increase of more than 50% in blood flow rate are obtained similarly to the case of microwave time and imitation sound time.

Skin Temperature

A temperature rise of about 3° C. was observed as a result of microwave radiation, and when the basic sequence was applied about 10 times by the apparatus of the invention, autosuggestion alone was enough to raise the skin temperature by 2.7° C. on an average.

Blood Pressure

Ten subjects exhibit a blood pressure lowering of 5 mm Hg in terms of systolic pressure during microwave radiation, and when temporary connection has been caused by the living body's reactions due to autosuggestion. The latter alone gave a systolic pressure lowering of 15 mm Hg on an average. In this case, persons with higher blood pressure exhibit more noticeable lowerings in blood pressure, while persons with lower blood pressure exhibit almost no drop in blood pressure, rather exhibiting a stabilized tendency.

Electrocardiogram

Subjects to whom the basic sequence have been applied 7-8 times exhibit a gradual decrease in the heart rate simply in response to autosuggestion and they exhibit a 10% decrease in the heart rate on an average. The height of R pulse waves decrease 15% on an average, and subjects with coronary insufficiency leading to ST depression exhibit decreased ST depression.

Respiration

When the apparatus of the invention is being in operation, it is observed that the type of respiration changes from thoracic to abdominal respiration. This means a change to a more stabilized type of respiration.

Brain Waves

Examinations during and after the use of the apparatus of the invention show that for persons with $\beta$ waves predominant, the waves sometimes change to $\alpha$ waves and for persons with $\alpha$ waves predominant, there is a tendency for the $\alpha$ wave potential to decrease and for the frequency to decrease also. For some subjects, $\alpha$ waves disappear while $\theta$ waves are observed to appear.

It is believed that these phenomena indicate that the cerebrum has relaxed its action, assuming a stabilized state close to sleep.

As is obvious from the results of the measurements described above, application of the basic training sequence by the apparatus of the invention causes the subject to exhibit reactions (realization of the contents of the message in a conditioned reflex fashion) and then enables him to control the autonomic nervous system with ease by his own will, thus easily mastering the autogenic training so as to cure his psychosomatic or similar disease by his own will without resorting to medicines or injections.

Thus, the invention incorporates a conditioned reflex mechanism in psychosomatic training, called the autogenic training, which in itself does not expect any physical operation to intervene therein, and systematizes the technical process leading to the mastering of the training. The apparatus of the invention is expected to open up a new field in psychosomatic therapeutics.

Figure 4:
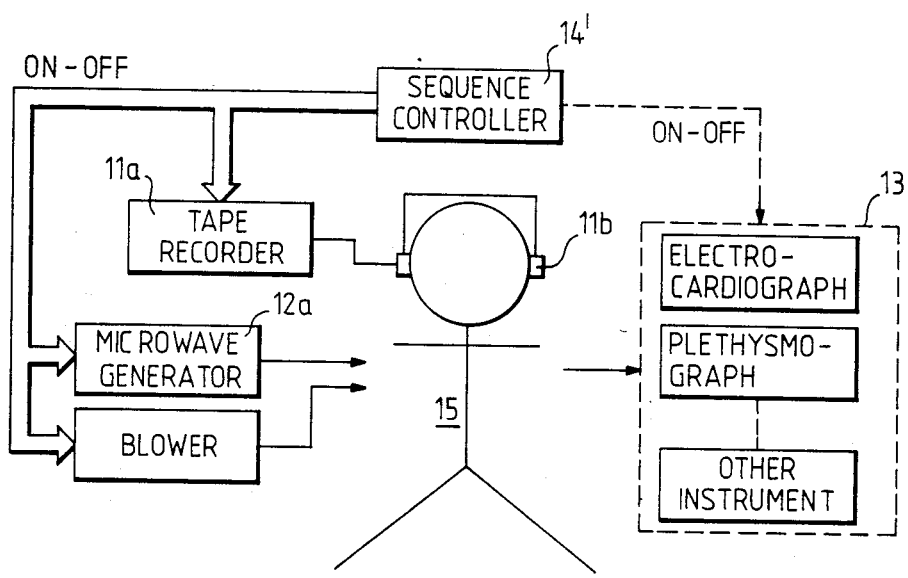
FIG. 4 is a block diagram showing an apparatus according to another embodiment of the invention.

FIG. 4 is a schematic view of an autogenic training and treating apparatus according to a second embodiment of the invention. This apparatus differs from the apparatus of FIG. 1 in that stimuli to be given to subjects comprise a therapeutic stimulus and a negative stimulus to slightly lessen the effect of said therapeutic stimulus and in that the stimulus notification signal is a clear or musical rhythm signal.

In FIG. 4, this apparatus comprises a tape recorder 11a and a headphone 11b, which form rhythm signal generating means, and a microwave generator 12a and a blower 12b with a suitable air flow rate, which form stimulus generating means, these components being driven under the control of a sequence controller 14'. In addition, where the stimulus sequence is applied to a subject 15 and his reactions (e.g., electrocardiogram and the blood flow rate of a local part) are measured, the measuring mechanism 13 therefore may be controlled by the sequence controller, as in the case of the aparatus of FIG. 1.

The tape recorder 11a has recorded therein music tuned to the rhythm of the stimulus cycle and in some cases it has also recorded therein a metronome sound to beat time to the rhythm. A record player may, of course, be used in place of the tape recorder. The headphone 11b is most preferable because it transmits only the reproduced sounds to the subject while shutting out the noise in the room, but it is also possible to install a speaker on top of the treating chair (not shown).

As for the microwave generator 12a and blower 12b serving as the stimulus generating means, the former is intended for heating the affected part by microwave radiation and the latter for cooling the affected part (skin) by air blowing, the relation between the two being such that when one is used as a generating source of stimuli having a therapeutic effect, the other is used as a negative stimulus generating source. The microwave generator 12a may be the stimulus generator 12 of the apparatus in FIG. 1, it is also possible to use in place thereof such heating means as infrared radiator.

Examples of the driving of the apparatus is connection with various diseases will now be described.

I. Vasodilative Stimulus Sequence

The purpose of this sequence is to cure diseases due to vasoconstriction, such as the stiffness of the shoulders, lumbago, and hypertension.

As for the therapeutic stimuli, use is made of microwaves, which are applied to the affected part of the subject for the purpose of heating on the principle of so-called high frequency heating, so as to dilate the constricted blood vessel. On the other hand, blowing air (room-temperature air, in the embodiment) against the affected part has, of course, the function of depriving the skin surface of its heat and thereby constricting the blood vessel.

Figure 5A:
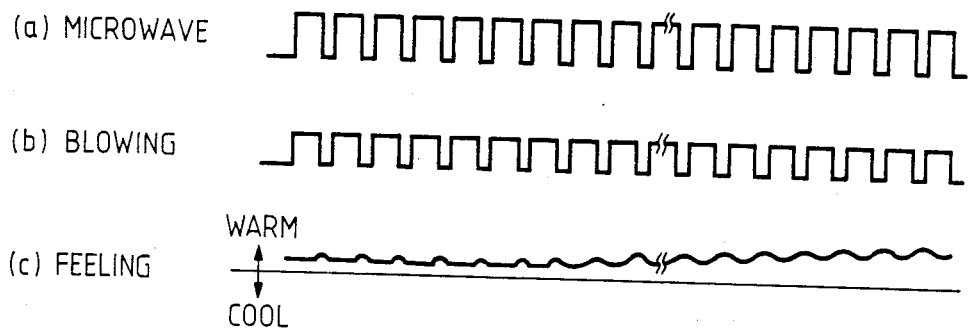
FIGS. 5A through 5C are sequence graphs in a case where the apparatus of FIG. 4 is driven in a vasodilation mode.
Figure 5B:
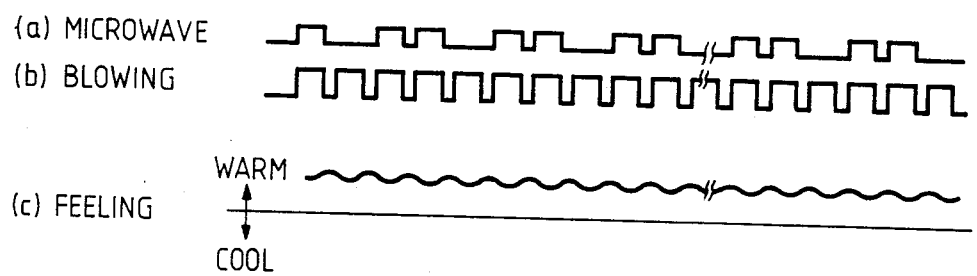
Figure 5C:
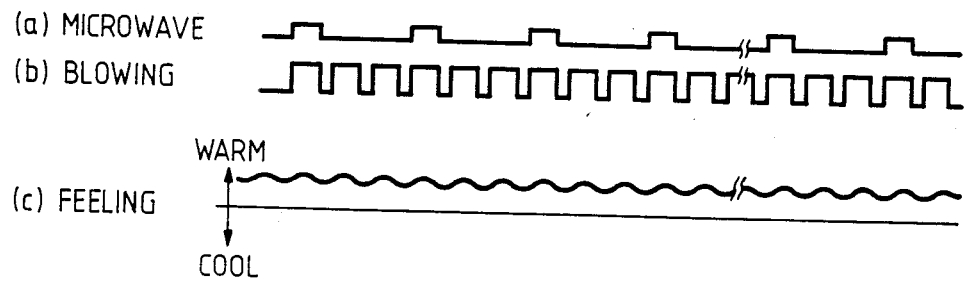

This sequence consists of 3 stages shown in FIGS. 5A–C. In the first stage (FIG. 5A), microwave radiation (a) which is therapeutic stimulation is applied to each of the affected parts (the shoulders, loins, etc.) for 3 seconds followed by a pause of 1 second, forming one cycle, such cycle being repeated 70 times (totaling about 280 seconds). In this case, air blowing (b) which is negative stimulation is effected concurrently with the generation of microwaves. As previously described, the intensity relation between the microwaves and air flow is such that the subject, who receives both, will feel somewhat warm as a whole. Such intermittent heating of the affected part provides a vasodilating tendency shown by the graph (c) in FIG. 5A. That is, the height of finger plethysmograph pulse waves (blood flow rate, and hence corresponding to changes in the inner diameter of the blood vessel) gradually increases, until it becomes stabilized in the latter half of this stage A. In addition, during the progress of the stimulation sequence, the subject listens to music with the rhythm corresponding to said cycle. When the stage A is over, the subject's autonomic nervous system has "learned" the rhythm consisting of 3 seconds of vasodilation (warm feeling) and 1 second of pause, and the next stage starts therefrom.

In the second stage (FIG. 5B), the microwave radiation (a) is thinned out such that one out of every three is omitted, and the microwave intensity is lower than that in the stage A. Thus, microwaves are radiated on two cycles and suspended on one cycle, and in this order they are intermittently radiated about 30 times (about 120 seconds). The degree of vasodilation as found by the finger plethysmograph pulse waves does not fall; rather it gradually rises throughout the stage B.

In the third stage (FIG. 5C), the microwave radiation (a) is omitted at a rate of ⅔ (radiation on one cycle and pause on two cycles), and the microwave intensity is the same as or lower than that in the stage B. In this stage C, radiation is effected 30 times (about 120 seconds). In this stage, the cold stimulation (air flow) is rather predominant than the warm or microwave stimulation, but the living body continues to regularly exhibit reactions indicating a warm feeling.

Application of the foregoing vasodilating sequence (stages A, B and C) to a subject suffering from, e.g., the stiffness of the shoulders provides localized vasodilation due to heating and attendant conditioned reflex during the treatment, thereby removing the peculiar dull pain or discomfortable feeling. After the treatment, recall of the stimulation rhythm of the sequence will cause the subject to exhibit the same reactions under normal room temperature as those he exhibited when subjected to the warm stimuli, since there is no cold stimulation of air flow as in the latter stage of the sequence.

II. Vasoconstrictive Stimulus Sequence

The purpose of this sequence is to cure diseases which can be cured by cooling the affected parts, such as nettle rash and headaches.

Accordingly, the therapeutic stimulus generator is in the form of a blower for blowing air to deprive the affected part of its heat so as to constrict the skin blood vessels. Particularly, this sequence is intended to change the control level of the autonomic nervous system to cause the subject to feel cold in spite of the fact that it is actually warm. In the case of nettle rash, a cure for which is cooling, this sequence is very effective in complete cure, (since it is impossible for the subject to stay in a cold place for a long time).

Figure 6A:
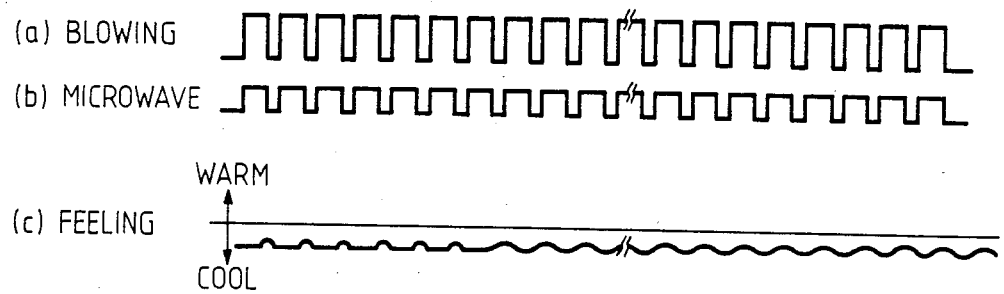
FIGS. 6A through 6C are sequence graphs in a case where the apparatus of FIG. 4 is driven in a vasoconstriction mode.
Figure 6B:
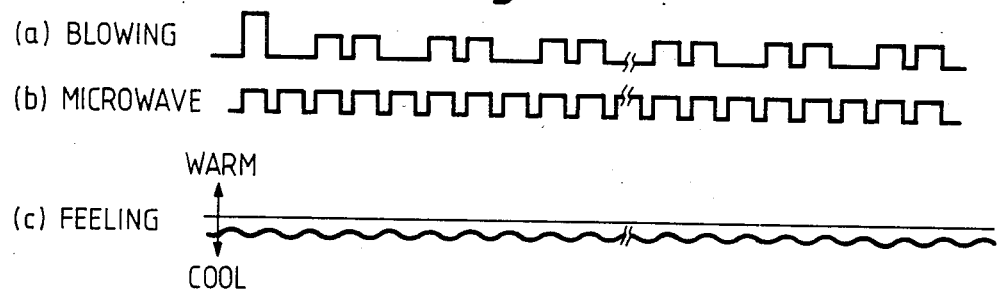
Figure 6C:
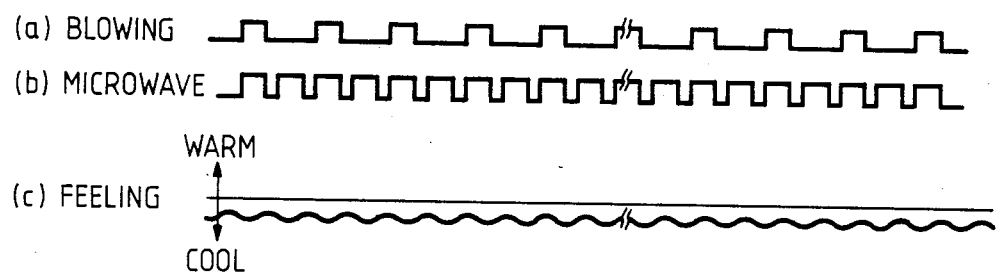

This vasoconstrictive stimulus sequence shown in FIGS. 6A–C is obtained by reversing the relation between microwaves and air flow in the vasodilating sequence of FIGS. 5A–C and is so arranged that when receiving both types of stimuli, subjects will feel somewhat cold; that is, the stimuli of air flow are predominant. In the stage A (FIG. 6A), both types of stimuli are regularly and concurrently applied about 100 times, and in the stage B (FIG. 6B) the air stimulation is omitted at a rate of ⅓ (blowing on 2 cycles and pause on 1 cycle, the air flow intensity being decreased) and several tens of cycles are performed. In the stage C (FIG. 6C), the air flow intensity is a little further decreased, and the omission rate is ½ (blowing on 1 cycle and pause on 1 cycle). The subject's feeling is as shown, it being seen that his body exhibits reactions of constant amplitude indicating cold throughout the 3 stages A–C.

In this case, too, the conditioned reflex established is reinforced so that after the treatment, even under room temperature conditions where the stimulus to the subject is the colder because of the absence of microwave radiation (heating), recall of the stimulus rhythm will bring about autonomic control (vasoconstriction).

This sequence is also very effective in curing nasal congestion, hypotension, etc.

While typical examples of the present inventive apparatus and of autogenic training sequences according to said apparatus have been described, they should not be construed as limiting the scope of the invention. The invention is defined only by the attached claims.

What is claimed is:

1. An autogenic training and treating apparatus comprising:
   signal generating means for giving a subject a notification signal,
   stimulus generating means for applying a stimulus to the subject's body, and
   sequence control means for driving said signal generating means and said stimulus generating means in a sequence in accordance with a sequence program, wherein said sequence program causes (a) said notification signal to be generated periodically throughout the sequence, (b) said stimulus to be generated during a first stage of the sequence in regular correspondence with said periodically generated signal, and (c) said stimulus to be generated during a second stage of said sequence only in intermittent correspondence with said periodically generated signal.

2. An apparatus as set forth in claim 1, wherein said sequence control means drives said signal generating means in such a manner as to generate said signal with a predetermined time duration and at predetermined intervals of time.

3. An apparatus as set forth in claim 1, wherein said sequence program is such that during said second stage, said stimulus is generated less frequently over time in correspondence with said periodically generated signal.

4. An apparatus as set forth in claim 1, wherein said signal generating means generates a signal containing a message which suggests a physical condition of the subject, and wherein said stimulus generating means generates a stimulus which enforces the physical condition suggested by said message.

5. An autogenic training and treating apparatus comprising:
   signal generating means for giving a subject a notification signal;
   stimulus generating means for applying a stimulus to the subject's body;
   sequence control means for driving said signal generating means and said stimulus generating means in accordance with a sequence program, wherein said sequence program causes (a) said signal to be generated periodically throughout the sequence program, (b) said stimulus to be generated in a first stage of the sequence in regular correspondence with said periodically generated signal, and (c) said stimulus in a second stage of the sequence to be only intermittently generated during the periods of generating said signal; and
   monitoring means for automatically measuring the reactions of said subject's body in correspondence with the progress of said sequence program.

6. An apparatus as set forth in claim 5, wherein the signal intermittently occurring in said sequence is generated with a predetermined time duration and at predetermined intervals of time.

7. A device as set forth in claim 5, wherein the frequency of generating said stimulus during said second stage in correspondence with said periodically generated signal decreases with time.

8. An apparatus as set forth in claim 5, wherein said reactions to be measured are selected from the group consisting of: brain waves, electrocardiogram, electric resistance of the skin, skin temperature, plethysmograph pulse waves, and electromyogram.

9. An apparatus as set forth in claim 5, wherein said signal generating means generates a signal containing a message suggesting a physical condition of the subject, and wherein said stimulus generating means generates a physical stimulus which enforces the physical condition suggested by said message.

10. An autogenic training and treating apparatus comprising:
    first stimulus generating means for applying a therapeutic stimulus to an affected part of a subject,
    second stimulus generating means for applying to the affected part of said subject a negative stimulus to lessen the effect of said therapeutic stimulus, and
    sequence control means for controlling said first and second stimulus generating means in first and second stages, wherein
    (a) in the first stage, the therapeutic stimulus and negative stimulus are simultaneously and intermittently generated in accordance with a constant rhythm and in such an intensity relation that the therapeutic effect of the former is predominant,
    (b) in the second stage, said therapeutic stimulus is intermittently omitted from the stimulus application cycle with said constant rhythm.

11. An apparatus as set forth in claim 10, wherein the intensity of the therapeutic stimulus in the second stage is lower than that in the first stage.

12. An apparatus as set forth in claim 10, wherein the frequency of omitting the therapeutic stimulus in the second stage is increased with time.

13. An apparatus as set forth in claim 10, wherein said therapeutic stimulus heats the affected part and wherein said negative stimulus cools the affected part.

14. An apparatus as set forth in claim 10, wherein said therapeutic stimulus cools the affected part and wherein said negative stimulus heats the affected part.

15. An autogenic training and treating apparatus comprising:
    rhythmic signal generating means for applying with a constant rhythm to a subject a notification signal
    first stimulus generating means for applying a therapeutic stimulus to an affected part of a subject,
    second stimulus generating means for applying to the affected part of said subject a negative stimulus to lessen the effect of said therapeutic stimulus, and
    sequence control means for controlling said first and second signal generating means in first and second stages, wherein
    (a) in the first stage, the therapeutic stimulus and negative stimulus are simultaneously and intermittently generated in accordance with a constant rhythm and in such an intensity relation that the therapeutic effect of the former is predominant,
    (b) in the second stage, said therapeutic stimulus is intermittently omitted from the stimulus application cycle.

16. An apparatus as set forth in claim 15, wherein the intensity of the therapeutic stimulus in the second stage is lower than that in the first stage.

17. An apparatus as set forth in claim 15, wherein the frequency of omitting the therapeutic stimulus in the second stage is increased with time.

18. An apparatus as set forth in claim 15, wherein said therapeutic stimulus heats the affected part and wherein said negative stimulus cools the affected part.

19. An apparatus as set forth in claim 15, wherein said therapeutic stimulus cools the affected part and wherein said negative stimulus heats the affected part.

20. An apparatus as set forth in claim 15, wherein said rhythm signal generating means produces a metronome sound and music having a similar rhythm.

* * * * *